United States Patent
Crone et al.

(10) Patent No.: US 8,680,353 B2
(45) Date of Patent: Mar. 25, 2014

(54) PROCESS FOR PREPARING OLIGOMERS OF BUTENE

(71) Applicants: Sven Crone, Limburgerhof (DE); Oliver Ryll, Edenkoben (DE); Till Blum, Singapore (SG); Alexander Weck, Freinsheim (DE); Rainer Papp, Speyer (DE); Roland Krokoszinski, Weisenheim a.Berg (DE); Heinrich-Josef Blankertz, Forst (DE)

(72) Inventors: Sven Crone, Limburgerhof (DE); Oliver Ryll, Edenkoben (DE); Till Blum, Singapore (SG); Alexander Weck, Freinsheim (DE); Rainer Papp, Speyer (DE); Roland Krokoszinski, Weisenheim a.Berg (DE); Heinrich-Josef Blankertz, Forst (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/680,910

(22) Filed: Nov. 19, 2012

(65) Prior Publication Data

US 2013/0131416 A1    May 23, 2013

Related U.S. Application Data

(60) Provisional application No. 61/561,951, filed on Nov. 21, 2011.

(51) Int. Cl.
- *C07C 1/00* (2006.01)
- *C07C 2/00* (2006.01)
- *C07C 4/00* (2006.01)
- *C07C 5/00* (2006.01)
- *C07C 6/00* (2006.01)

(52) U.S. Cl.
USPC .......................................... 585/329; 585/517

(58) Field of Classification Search
USPC .......... 585/324, 329, 502, 510, 511, 517, 520
See application file for complete search history.

(56) References Cited

U.S. PATENT DOCUMENTS

| | | | | |
|---|---|---|---|---|
| 5,849,972 A | * | 12/1998 | Vicari et al. | 585/531 |
| 6,444,866 B1 | * | 9/2002 | Commereuc et al. | 585/517 |

(Continued)

FOREIGN PATENT DOCUMENTS

| | | |
|---|---|---|
| DE | 199 22 038 A1 | 11/2000 |
| EP | 0 149 145 A2 | 7/1985 |

(Continued)

OTHER PUBLICATIONS

International Preliminary Report on Patentability and Written Opinion issued Feb. 13, 2013 in PCT/EP2012/071106 with English translation of categories of cited documents filed Oct. 25, 2012.

*Primary Examiner* — Walter D Griffin
*Assistant Examiner* — Jelitza Perez
(74) *Attorney, Agent, or Firm* — Oblon, Spivak, McClelland, Maier & Neustadt, L.L.P.

(57) ABSTRACT

A process for preparing oligomers by continuous oligomerization of butenes is described, wherein a) a feed stream 1) comprising 1-butene and 2-butene in a total concentration of from 10 to 70% by weight and from 10 to 60% by weight of isobutane is reacted until more than 60% by weight of the 1-butene comprised in the feed stream 1 but less than 50% by weight of the 2-butene comprised in feed stream 1 have been converted into oligomers. b) The oligomers obtained in a) are separated off and optionally passed to a further work-up and the remaining residual stream is fed to work-up by distillation. c) Isobutane is separated off by distillation from the residual stream, and d) the isobutane-depleted stream obtained after the work-up by distillation c) is reacted to form oligomers.

14 Claims, 1 Drawing Sheet

(56) References Cited

U.S. PATENT DOCUMENTS

| | | | |
|---|---|---|---|
| 6,689,927 B1 * | 2/2004 | Frame et al. | 585/510 |
| 6,846,965 B1 * | 1/2005 | Schulz et al. | 585/510 |
| 6,852,898 B2 * | 2/2005 | Schulz et al. | 585/531 |
| 7,161,054 B2 * | 1/2007 | Heidemann et al. | 585/531 |
| 7,381,853 B2 * | 6/2008 | Martens et al. | 585/1 |
| 2005/0182284 A1 * | 8/2005 | Stanat et al. | 585/535 |

FOREIGN PATENT DOCUMENTS

| | | |
|---|---|---|
| EP | 1 724 249 A2 | 11/2006 |
| WO | WO 95/14647 A1 | 6/1995 |
| WO | WO 00/69795 A1 | 11/2000 |

* cited by examiner

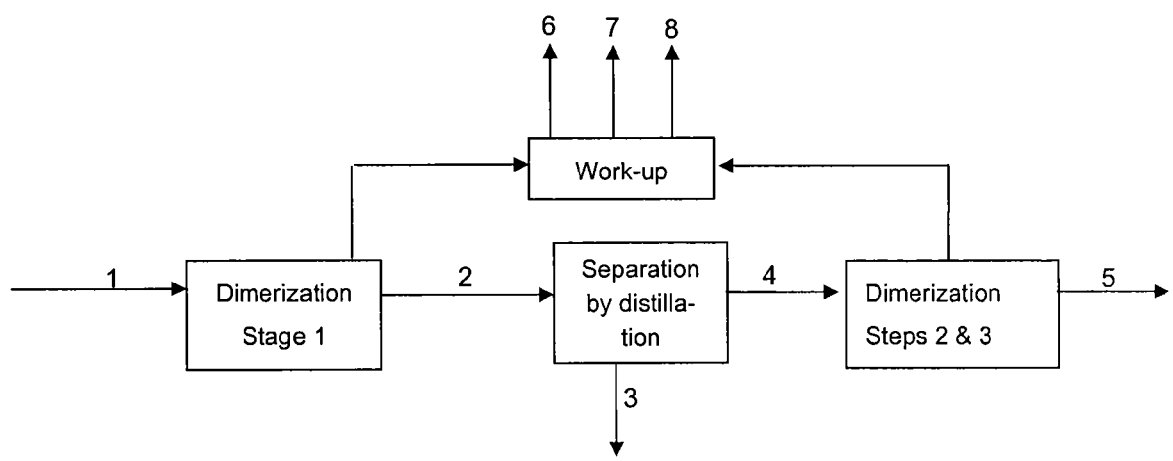

PROCESS FOR PREPARING OLIGOMERS OF BUTENE

The invention relates to a process for preparing oligomers by continuous oligomerization of butenes, wherein
a) a feed stream comprising 1-butene and 2-butene in a total concentration of from 10 to 70% by weight and from 10 to 60% by weight of isobutane is used (hereinafter referred to as feed stream 1),
b) this feed stream 1 is reacted until more than 60% by weight of the 1-butene comprised in the feed stream 1 but less than 50% by weight of the 2-butene comprised in feed stream 1 have been converted into oligomers,
c) the oligomers obtained in b) are separated off and optionally passed to a further work-up and the remaining residual stream is fed to work-up by distillation,
d) isobutane is separated off by distillation from the residual stream,
e) the isobutane-depleted stream obtained after the work-up by distillation d) (hereinafter referred to as feed stream 2) is reacted to form oligomers.

Oligomers of butene, for example octenes and dodecenes, are of great importance as starting materials for further chemical syntheses and as constituents of fuels such as gasoline, diesel or kerosene. Thus, these oligomers are, for example, converted by hydroformylation and subsequent hydrogenation into alcohols. The alcohols obtained are suitable for producing plasticizers and surfactants.

Processes for oligomerizing butenes are known. WO 00/69795 describes an oligomerization process in which the oligomerization is carried out in a plurality of stages, i.e. in a plurality of successive adiabatically operated reaction zones, over a heterogeneous, nickel-comprising oligomerization catalyst.

The streams used for an oligomerization should have a very high content of linear butenes. A content of inert butanes reduces the space-time yield.

According to EP-A 1724 249, n-butane and isobutane are therefore separated off by means of a multistage process before carrying out the oligomerization. The multistage process comprises an extractive distillation, a work-up of the resulting bottoms by distillation and scrubbing of the overhead fraction.

The separation of butenes and butanes by extractive distillation is also described, for example, in EP-A 149145.

The oligomerization of butenes can be carried out using raffinate 2 streams which are taken off from steam crackers or refineries or are available as end products of other chemical processes, dehydrogenations or MTO (methanol to olefins) processes. Raffinate 2 streams are essentially C4 streams.

Butadiene and isobutene are generally mostly removed by means of preceding process steps from such raffinate 2 streams. Known methods for separating off butadiene are plants for extraction of butadiene or the selective hydrogenation of butadiene to butenes.

Raffinate 2 streams from refineries generally comprise significantly smaller amounts of 1- and 2-butenes suitable for oligomerization than those from steam crackers.

In the case of a low content of butenes in the raffinate 2 streams, the reactors and the work-up section of the oligomerization have to be made appropriately large in order to achieve a satisfactory yield of oligomers and effective utilization of the linear butenes comprised in the raffinate.

It is therefore desirable to have a simple and effective process in which streams having a low content of linear butenes, e.g. raffinate 2 streams from refineries, can also be oligomerized with a high space-time yield. In particular, the linear butenes available and the capacity of the reactors and work-up sections should be able to be used very optimally.

It was therefore an object of the present invention to provide such a process.

We have accordingly found the process defined at the outset.

Embodiments of the process of the invention are described below.

a)

A suitable feed stream 1 comprises predominantly hydrocarbons having 4 carbon atoms (C4-hydrocarbons) and in particular comprises more than 85% by weight, preferably more than 95% by weight, particularly preferably more than 99% by weight, of C4-hydrocarbons.

Possible streams having such a C4-hydrocarbon content are, for example, raffinate 2 streams which can be taken off from steam crackers or refineries or are available as end products of other chemical processes.

Feed stream 1 preferably comprises no or only small amounts of butadiene and isobutene. Insofar as these are originally present, they are generally most removed by means of preceding process steps. Known methods of separating off butadiene are plants for extraction of butadiene or the selective hydrogenation of butadiene to butenes.

Isobutene can, for example, be separated off by preparation of methyl tert-butyl ether (MTBE) or isobutyl tert-butyl ether (IBTBE) with subsequent redissociation.

Weights indicated below are based on the total weight of the feed stream 1.

The feed stream 1 preferably comprises less than 3% by weight, in particular less than 1% by weight, particularly preferably less than 0.3% by weight, of butadiene.

The feed stream 1 preferably comprises less than 3% by weight, in particular less than 1% by weight, particularly preferably less than 0.3 or less than 0.1% by weight, of isobutene.

Feed stream 1 comprises 1-butene and 2-butene in a total amount of from 10 to 70% by weight.

1-Butene and 2-butene are linear butenes having the double bond in the 1,2 and 2,3, respectively, position.

Feed stream 1 preferably comprises 1-butene and 2-butene in a total concentration of from 20 to 60% by weight, particularly preferably in a total concentration of 30 to 60% by weight, very particularly preferably in a total concentration of from 40 to 60% by weight.

Feed stream 1 comprises both 1-butene and 2-butene.

Feed stream 1 preferably comprises
from 1 to 30% by weight of 1-butene and from 1 to 40% by weight of 2-butene
particularly preferably
from 5 to 30% by weight of 1-butene and from 5 to 40% by weight of 2-butene,
where the total amount of the two butenes is from 10 to 70% by weight or from 20 to 60% by weight.

Very particular preference is given to the content of 1-butene being from 5 to 30% by weight and that of 2-butene being from 20 to 40% by weight, with the total content of the 2 butenes being from 40 to 60% by weight.

Feed stream 1 comprises from 10 to 60% by weight of isobutane, in particular from 15 to 50% by weight and particularly preferably from 20 to 50% by weight of isobutane. In a very particularly preferred embodiment, feed stream 1 comprises isobutane in an amount of from 30 to 50% by weight.

Apart from 1-butene, 2-butene, isobutane, feed stream 1 can comprise n-butane and further constituents, including, for example, possibly small amounts of butadiene, isobutene (see above) or impurities.

In particular, feed stream 1 also comprises n-butane, e.g. in an amount of from 0 to 60% by weight, in particular from 5 to 60% by weight, preferably from 5 to 30% by weight.

Feed stream 1 preferably consists in toto of
from 1 to 30% by weight of 1-butene
from 1 to 35% by weight of 2-butene
from 10 to 60% by weight of isobutane
from 0 to 60% by weight of n-butane
from 0 to 10% by weight of further constituents.

Feed stream 1 particularly preferably consists in toto of
from 5 to 30% by weight of 1-butene
from 5 to 35% by weight of 2-butene
from 15 to 60% by weight of isobutane
from 5 to 60% by weight of n-butane
from 0 to 5% by weight of further constituents.

Feed stream 1 very particularly preferably consists in toto of
from 5 to 30% by weight of 1-butene
from 20 to 40% by weight of 2-butene
from 20 to 50% by weight of isobutane
from 5 to 30% by weight of n-butane
from 0 to 2% by weight of further constituents.

In a particular embodiment, feed stream 1 consists in toto of
from 10 to 30% by weight of 1-butene
from 20 to 40% by weight of 2-butene
from 30 to 50% by weight of isobutane
from 5 to 20% by weight of n-butane
from 0 to 2% by weight of further constituents.

b)

In process step b), an oligomerization is carried out. For the present purposes, the term oligomerization encompasses a dimerization. In the oligomerization, 1-butene and 2-butene are converted into octenes (dimerization) or further into dodecenes (trimerization) or higher oligomers (C16 or more, referred to as C16+ for short).

Octenes formed in the dimerization are virtually exclusively isooctenes, i.e., for example, singularly, doubly or triply branched C8-olefins (e.g. 3-methylheptene or 3,4-dimethylhexene). Correspondingly, virtually exclusively isododecenes are formed as trimers.

For this reason, the term octene comprises, for the purposes of the present patent application, octenes of any type and in particular octene mixtures as are formed in the oligomerization, i.e. mixtures consisting essentially of various isooctenes.

Correspondingly, the term dodecene comprises, for the purposes of the present patent application, dodecenes of any type and in particular dodecene mixtures as are formed in the oligomerization, i.e. mixtures consisting essentially of various isododecenes.

Oligomerization processes are known and are described, for example, in EP-A 1724 249 or WO 00/69795.

The oligomerization is preferably carried out in the presence of a heterogeneous catalyst.

Possible heterogeneous catalysts are, for example, acid catalysts.

Preference is given to nickel-comprising heterogeneous catalysts, with particular preference being given to nickel in the form of nickel oxide (NiO). Apart from NiO, the heterogeneous catalyst can comprise further constituents, e.g. $SiO_2$, $TiO_2$, $ZrO_2$ or $Al_2O_3$ as support material.

The oligomerization in process step b) can be carried out in one reaction zone or in a plurality of reaction zones collected in parallel or in series.

The oligomerization is preferably carried out at temperatures of from 30 to 180° C., particularly preferably at temperatures of from 30 to 140° C.

The oligomerization is preferably carried out at pressures of from 10 to 300 bar, particularly preferably at pressures of from 15 to 100 bar.

Suitable reactors are, for example, cylindrical reactors charged with the catalyst. The preferably liquid feed mixture 1 flows through these from the top downward or vice versa. In the case of a plurality of reaction zones, reactors connected in series or in parallel or a reactor divided appropriately into a plurality of reaction zones are/is correspondingly used.

The oligomerization in process step b) is preferably carried out in only one reaction zone.

1-Butenes, which have a higher reactivity, are reacted first in the oligomerization.

In process step b), feed stream 1 is reacted until more than 60% by weight of all 1-butenes comprised in feed stream 1 but less than 50% by weight of the 2-butenes comprised in feed stream 1 have been converted into oligomers.

Feed stream 1 is preferably reacted in process step b) until more than 80% by weight of all 1-butenes comprised in feed stream 1 but less than 50% by weight of the 2-butenes comprised in feed stream 1 have been converted into oligomers.

Feed stream 1 is particularly preferably reacted in process step b) until more than 85% by weight of all 1-butenes comprised in feed stream 1 but less than 35% by weight of the 2-butenes comprised in feed stream 1 have been converted into oligomers.

Feed stream 1 is very particularly preferably reacted in process step b) until more than 85% by weight of all 1-butenes comprised in feed stream 1 but less than 25% by weight of the 2-butenes comprised in feed stream 1 have been converted into oligomers.

The conversion of 1-butene and 2-butene attained can easily be determined by gas-chromatographic quantification of the remaining amount of 1- and 2-butene.

c)

Process step c) is the isolation of the oligomers formed in b).

The oligomers are preferably separated off by distillation, with the oligomers being discharged in the bottoms and the C4 fraction being taken off at the top.

The oligomers are passed to a further work-up. Here, in particular, a separation into the fractions octene, dodecene and C16+ is carried out. The fractionation can be carried out in a known way by distillation.

The remaining residual stream is fed to a work-up by distillation, as described under process step d).

d)

In process step d), isobutane is separated off from the residual stream by distillation.

The total amount of the residual stream obtained in c) and then to be distilled in d) is preferably from 5 to 95% by weight, in particular from 30 to 95% by weight, particularly preferably from 50 to 90% by weight and very particularly preferably from 60 to 85% by weight, of the feed stream 1.

In particular, the residual stream consists in toto of
from 10 to 60% by weight of 2-butene
from 1 to 30% by weight of 1-butene
from 20 to 70% by weight of isobutane
from 1 to 40% by weight of n-butane
from 0 to 10% by weight of other constituents.

The residual stream particularly preferably consists in toto of
from 20 to 50% by weight of 2-butene
from 1 to 20% by weight of 1-butene from 3 to 60% by weight of isobutane
from 1 to 30% by weight of n-butane
from 0 to 5% by weight of other constituents.

The residual stream very particularly preferably consists in toto of
from 30 to 40% by weight of 2-butene
from 1 to 10% by weight of 1-butene
from 40 to 55% by weight of isobutane
from 10 to 20% by weight of n-butane
from 0 to 5% by weight of other constituents.

The distillation in process step d) can be carried out by known methods.

To separate off the isobutane, it is not necessary to carry out an extractive distillation. In a preferred embodiment, the distillation is therefore not an extractive distillation and no extractant is added. Preference is given to no solvent at all being added in process step d).

The distillation is preferably carried out at temperatures at the top of from 50 to 90° C., particularly preferably from 60 to 80° C. and very particularly preferably from 65 to 75° C., and at temperatures at the bottom of from 60 to 110° C., particularly preferably from 70 to 100° C. and very particularly preferably from 80 to 90° C.

The distillation is preferably carried out at pressures at the bottom of from 8 to 15 bar, particularly preferably from 9 to 13 bar and very particularly preferably from 10 to 12 bar. The pressure drop over the entire column can be, for example, 0.1-0.5 bar.

Suitable distillation columns are both packed columns and columns having built-in column trays (tray columns). Columns comprising both packing and trays, e.g. beds of packing elements in parts of the column and appropriate internals (steel plates) in other parts, are also suitable. Preference is given to a tray column. The tray column can comprise, for example, from 40 to 150, in particular from 80 to 120, trays.

The distillation column can preferably comprise at least 5, in particular at least 10, theoretical plates. The total number of theoretical plates can, for example, be from 10 to 100, in particular from −20 to 100 or from 30 to 100. In a particular embodiment, the distillation column comprises a total of 40-70 theoretical plates. In a preferred embodiment, the column is divided into a stripping section and an enrichment section; the stripping section can comprise, for example, 25-40 theoretical plates and the enrichment section can comprise 15-30 theoretical plates.

Preference is given to more than 60% by weight, in particular more than 70% by weight, particularly preferably more than 75% by weight and very particularly preferably more than 80% by weight, of the isobutane comprised in the residual stream being separated off by means of the distillation.

The isobutane separated off and any further compounds separated off (hereinafter referred to collectively as waste stream) are preferably condensed and can be used for other purposes.

The waste stream consists, in particular, of
from 50 to 100% by weight of isobutane
from 0 to 20% by weight of n-butane
from 0 to 20% by weight of 2-butene
from 0 to 20% by weight of 1-butene
from 0 to 5% by weight of other constituents.

The waste stream particularly preferably consists of
from 70 to 95% by weight of isobutane
from 0 to 10% by weight of n-butane
from 0 to 10% by weight of 2-butene
from 0 to 10% by weight of 1-butene
from 0 to 5% by weight of other constituents.

The waste stream very particularly preferably consists of
from 80 to 95% by weight of isobutane,
from 0 to 8% by weight of n-butane
from 0 to 8% by weight of 2-butene
from 0 to 8% by weight of 1-butene
from 0 to 1% by weight of other constituents.

This leaves a mixture which is rich in 2-butene and can preferably be taken off at the bottom of the columns. This mixture is fed again as feed stream 2 to an oligomerization.

In a particular embodiment, process steps c) and d) can be carried out in a joint distillation column. Here, the oligomers (octane and higher oligomers) are obtained as bottom product, feed stream 2 (butene-rich stream) is discharged as side offtake stream and the remaining waste stream (butane-rich stream) is taken off at the top.

e)

The feed stream 2 obtained in d) is reacted again to form oligomers in process step e).

Feed stream 2 preferably comprises more than 40% by weight, in particular more than 50% by weight and very particularly preferably more than 60% by weight, of 2-butene.

Feed stream 2 preferably consists in toto of from 40 to 80% by weight of 2-butene
from 0 to 20% by weight of 1-butene
from 1 to 20% by weight of isobutane
from 5 to 50% by weight of n-butane
from 0 to 10% by weight of other constituents.

Feed stream 2 particularly preferably consists in toto of
from 50 to 80% by weight of 2-butene
from 0 to 10% by weight of 1-butene
from 1 to 10% by weight of isobutane
from 10 to 40% by weight of n-butane
from 0 to 5% by weight of other constituents.

Feed stream 2 very particularly preferably consists in toto of
from 60 to 70% by weight of 2-butene
from 0 to 5% by weight of 1-butene
from 1 to 10% by weight of isobutane
from 20 to 40% by weight of n-butane
from 0 to 2% by weight of other constituents.

What has been said above under b) for carrying out the oligomerization applies analogously here.

What has been said above with regard to the work-up of the oligomers obtained also applies analogously.

In a preferred embodiment, the work-up of the oligomers obtained in b) is carried out together with that of the oligomers obtained in e). In a preferred embodiment, the oligomers from b) and from e) are fed to a joint distillation for separation into octane, dodecene and C16+.

The total oligomers obtained in the process steps b) and e) are preferably a mixture of
from 70 to 100% by weight, in particular from 75 to 90% by weight, of octene
from 0 to 30% by weight, in particular from 5 to 20% by weight, of dodecene
from 0 to 20% by weight, in particular from 1 to 10% by weight, of C16+,
based on the total amount of all oligomers formed in b) and e).

The oligomerization under e) leaves, as residue, a mixture which is rich in n-butane and preferably comprises 1-butene and 2-butene in a total amount of less than 25% by weight, particularly preferably less than 20% by weight. This mixture can be used for other purposes.

The process of the invention is a continuous process and all above process steps are therefore preferably operated continuously.

It is an advantage of the process of the invention that streams having a low content of linear butenes (1-butene and 2-butene), e.g. raffinate 2 streams from refineries, can be oligomerized with a high space-time yield. The capacity of the reactors and work-up sections can be utilized optimally here.

The process of the invention enables the total 1- and 2-butenes comprised in feed stream 1 to be converted to an extent of more than 85% by weight, in particular more than 90% by weight, into oligomers.

It is a further advantage of the process of the invention that it can also easily be carried out in existing oligomerization plants. In general, only few modifications of the apparatus are necessary for this purpose. The process of the invention therefore allows flexible adaptation to various raw material sources. In particular, in the case of a change from C4 sources having a high content of butenes to C4 sources having a low content of butenes, the apparatus can be adapted easily and the process of the invention can readily be carried out.

EXAMPLES

Two simulations of a butene dimerization were carried out. Under otherwise identical boundary conditions, i.e. the same feed stream, identical apparatuses (reactors and apparatuses of the work-up section), the composition of all subsequent streams and finally the yield of octene were calculated. A commercially available program which can be obtained under the name aspen plus from aspentech was used for this purpose.

Example According to the Invention

A process in which the feed stream is oligomerized in a 1st stage and oligomers are separated off (process steps a, b and c), isobutane is separated off by distillation from the residual stream (process step d) and the resulting low-isobutane stream is again oligomerized (process step e), with the oligomerization in e) being carried out in two stages, was simulated. The oligomers obtained in the oligomerizations are passed to a joint work-up in which the oligomers are separated into octene, dodecene and higher oligomers (C16 and higher oligomers, referred to collectively as C16+).

This process is shown in the FIGURE. The calculated total amount and composition of the individual streams are indicated below. The numbering of the streams corresponds to the numbering in the FIGURE. The total amount is reported in metric tons/hour, percentages are percent by weight.

| Stream 1 | |
|---|---|
| Total amount | 52.5 t/h |
| n-Butane | 11.6% |
| Isobutane | 36.0% |
| 1-Butene | 22.7% |
| 2-Butene | 29.3% |
| Impurities | 0.4% |

| Stream 2 | |
|---|---|
| Total amount | 39.7 t/h |
| n-Butane | 15.3% |
| Isobutane | 47.6% |
| 1-Butene | 2.5% |
| 2-Butene | 34.1% |
| Impurities | 0.5% |

| Stream 3 | |
|---|---|
| Total amount | 20.2 t/h |
| n-Butane | 3.6% |
| Isobutane | 88.7% |
| 1-Butene | 3.4% |
| 2-Butene | 4.1% |
| Impurities | 0.2% |

| Stream 4 | |
|---|---|
| Total amount | 19.4 t/h |
| n-Butane | 27.6% |
| Isobutane | 5.0% |
| 1-Butene | 1.7% |
| 2-Butene | 65.5% |
| Impurities | 0.2% |

| Stream 5 | |
|---|---|
| Total amount | 7.0 t/h |
| n-Butane | 76.9% |
| Isobutane | 13.9% |
| 1-Butene | 0.5% |
| 2-Butene | 8.3% |
| Impurities | 0.4% |

Stream 6 (more than 99.9% of octene): 20.2 t/h
Stream 7 (more than 99.9% of dodecene): 3.9 t/h
Stream 8 (more than 99.9% of C16+): 1.1 t/h Comparative Example For comparison, a process in which no removal of the isobutane by distillation is carried out was calculated. In the FIGURE, stream 3 therefore no longer occurs and streams 2 and 4 become identical.

| Stream 1 | |
|---|---|
| Total amount | 52.5 t/h |
| n-Butane | 11.6% |
| Isobutane | 36.0% |
| 1-Butene | 22.7% |
| 2-Butene | 29.3% |
| Impurities | 0.4% |

| Stream 2 = Stream 4 | |
|---|---|
| Total amount | 39.5 t/h |
| n-Butane | 15.4% |
| Isobutane | 47.8% |

-continued

| Stream 2 = Stream 4 | |
| --- | --- |
| 1-Butene | 2.5% |
| 2-Butene | 33.9% |
| Impurities | 0.4% |

| Stream 5 | |
| --- | --- |
| Total amount | 28.7 t/h |
| n-Butane | 21.2% |
| Isobutane | 65.8% |
| 1-Butene | 0.7% |
| 2-Butene | 12.0% |
| Impurities | 0.3% |

Stream 6 (more than 99.9% of octene): 18.6 t/h
Stream 7 (more than 99.9% of dodecene): 4.0 t/h
Stream 8 (more than 99.9% of C16+): 1.2 t/h A yield increase of 8.6% of octene can therefore be achieved when the separation by distillation is carried out (see stream 6 of 20.2 t/h in the example according to the invention).

The invention claimed is:

1. A process for preparing oligomers by continuous oligomerization of butenes, comprising
   a) reacting a feed stream 1) comprising 1-butene and 2-butene in a total concentration of from 10 to 70% by weight and from 20 to 60% by weight of isobutane until more than 60% by weight of the 1-butene comprised in the feed stream 1 but less than 50% by weight of the 2-butene comprised in feed stream 1 have been converted into oligomers,
   b) separating off the oligomers obtained in a) and optionally passing to a further work-up and the remaining residual stream is fed to work-up by distillation,
   c) separating off the isobutane by distillation from the remaining residual stream,
   d) reacting an isobutane-depleted stream obtained after the work-up by distillation c) (hereinafter referred to as feed stream 2) to form oligomers
   wherein feed stream 1) and feed stream 2) are different.

2. The process according to claim 1, wherein the feed stream 1) comprises 1 butene and 2-butene in a total concentration of from 30 to 60% by weight.

3. The process according to claim 2, wherein feed stream 1 comprises from 5 to 30% by weight of 1-butene and from 20 to 40% by weight of 2-butene.

4. The process according to claim 1, wherein feed stream 1 comprises from 30 to 50% by weight of isobutane.

5. The process according to claim 1, wherein the feed stream 1 is reacted in a) until more than 80% by weight of the 1-butene comprised in feed stream 1 but less than 50% by weight of the 2-butene are converted into oligomers.

6. The process according to claim 1, wherein the total amount of the remaining residual stream is from 5 to 95% by weight of feed stream 1.

7. The process according to claim 1, wherein the remaining residual stream consists of
   from 30 to 40% by weight of 2-butene
   from 1 to 10% by weight of 1-butene
   from 40 to 55% by weight of isobutane
   from 10 to 20% by weight of n-butane
   from 0 to 5% by weight of other constituents.

8. The process according to claim 1, wherein process step c) is not an extractive distillation.

9. The process according to claim 1, wherein more than 80% by weight of the isobutane are separated off from the remaining residual stream in process step c).

10. The process according to claim 1, wherein the feed stream 2 obtained after process step c) consists of
    from 60 to 70% by weight of 2-butene
    from 0 to 5% by weight of 1-butene
    from 1 to 10% by weight of isobutane
    from 20 to 40% by weight of n-butane
    from 0 to 2% by weight of other constituents.

11. The process according to claim 1, wherein the oligomers from the oligomerizations a) and d) are passed to a joint work-up.

12. The process according to claim 1, wherein the total 1- and 2-butene comprised in feed stream 1 are converted to an extent of more than 90% by weight into oligomers.

13. The process according to claim 1, wherein the total oligomers obtained are a mixture of
    from 70 to 100% by weight of octene
    from 0 to 30% by weight of dodecene
    from 0 to 20% by weight of higher oligomers.

14. The process according to claim 1, wherein the remaining residual stream consists of
    from 10 to 60% by weight of 2-butene
    from 1 to 30% by weight of 1-butene
    from 20 to 70% by weight of isobutane
    from 1 to 40% by weight of n-butane
    from 0 to 10% by weight of other constituents.

* * * * *